Figure 1:
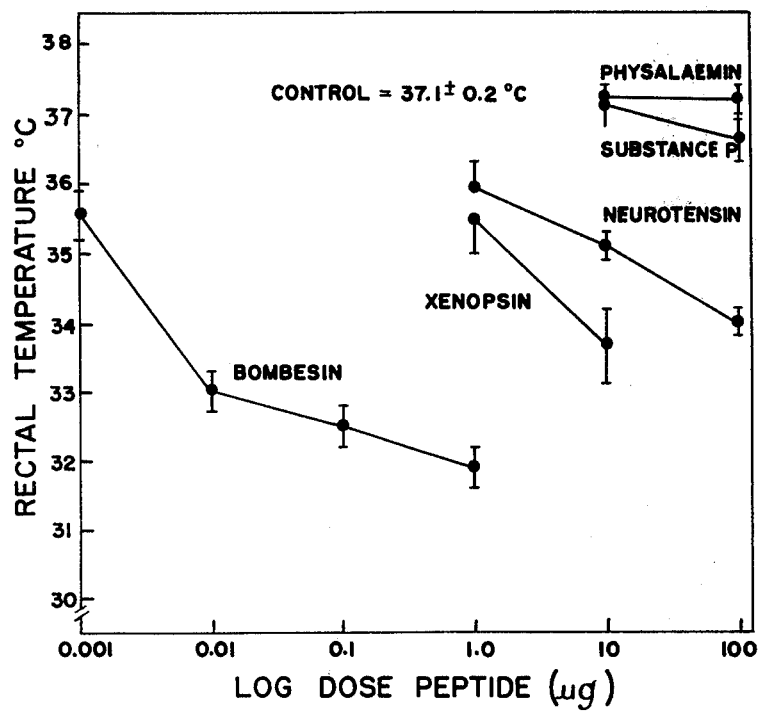

United States Patent [19]

Brown et al.

[11] 4,207,311
[45] Jun. 10, 1980

[54] PEPTIDES HAVING ANALGESIC AND THERMOREGULATIVE PROPERTIES

[75] Inventors: Marvin R. Brown; Jean E. F. Rivier; Wylie W. Vale, Jr., all of La Jolla, Calif.

[73] Assignee: The Salk Institute for Biological Studies, San Diego, Calif.

[21] Appl. No.: 856,126

[22] Filed: Nov. 30, 1977

Related U.S. Application Data

[63] Continuation-in-part of Ser. No. 816,441, Jul. 18, 1977, abandoned.

[51] Int. Cl.$^2$ .................... A61K 37/00; C07C 103/52
[52] U.S. Cl. .............................. 424/177; 260/112.5 R
[58] Field of Search .................. 260/112.5 R; 424/177

[56] References Cited
PUBLICATIONS

A. Anastasi, et al., Archives of Biochemistry and Biophysical 148, 443–446 1972.
Chem. Pharm. Bulletin 21 (6) 1388–1391 (1973).

*Primary Examiner*—Delbert R. Phillips
*Attorney, Agent, or Firm*—Fitch, Even & Tabin

[57] ABSTRACT

Peptides having thermoregulative properties when administered to animals. The peptides are identified by the structure:

$R_1$-$R_2$-Trp-Ala-Val-$R_3$-His-$R_4$-$R_5$-$NH_2$ wherein: $R_1$ is selected from the group consisting of hydrogen, an amino acid selected from the group consisting of p-Glu,Gln,Arg,Leu,Gly,Asn,Thr,Val, and Pro, and peptides having from 2 to 6 amino acids wherein the amino acids are selected from p-Glu,Gln,Arg,Leu,Gly,Asn,Thr,Val, and Pro, provided that when p-Glu is part of $R_1$, p-Glu is located at the N terminus of the peptide; $R_2$ is selected from the group consisting of D-pGlu, D-Gln and Gln; $R_3$ is selected from the group consisting of D-Ala and Gly; $R_4$ is selected from the group consisting of Phe and Leu and $R_5$ is selected from Met and D-Met. Intermediates of the peptides are also provided.

31 Claims, 2 Drawing Figures

PEPTIDES HAVING ANALGESIC AND THERMOREGULATIVE PROPERTIES

The invention described herein was made in the course of work under a grant or award from the Department of Health, Education, and Welfare.

The present application is a continuation in part of application Ser. No. 816,441, filed July 18, 1977, now abandoned.

The present invention relates generally to peptides useful for thermoregulation of the body temperature of mammals, including humans. More particularly, the present invention is directed to a method for the reduction of core temperature in mammals by the intracisternal injection of a particular peptide.

The thermoregulation of body temperature of mammals is of great importance to the medical profession. Certain types of operations, particularly heart operations, are desirably performed with lowered body temperature. Certain physiological disorders result in malfunctioning of the thermoregulative function of the body resulting in increased and uncontrollable body temperatures. It would be desirable to provide a pharmaceutically effective composition which can be used to reduce the body temperature either from an undesirably high temperature or in preparation for medical treatment.

The tridecapeptide, neurotensin, has been isolated and characterized from bovine hypothalamus. Neurotensin has the structure:

p-Glu-Leu-Tyr-Glu-Asn-Lys-Pro-Arg-Arg-Pro-Tyr-Ile-Leu-OH Neurotensin has been reported to have a body temperature lowering effect; G. Bissette et al, Nature 262: 607 (1976). In the studies reported in the G. Bissette et al article, neurotensin given intracisternally, but not intravenously, produced a lowering of basal body temperature of mice at room temperature or exposed to cold (4° C.). However, the body temperature lowering effect of neurotensin is not sufficient for practical pharmaceutical and operative use. It would be desirable to provide peptide compositions which are more effective for both inducing hypothermia and for treating hypothermia.

Accordingly, it is a principal object of the present invention to provide a method for lowering body temperatures of mammals.

It is another object of the present invention to provide peptide compositions which have a body temperature lowering effect and to provide a method for use of the peptides.

It is a further object of the present invention to provide peptide compositions which have thermoregulative properties and analgesic and/or anesthetic properties.

These and other objects of the invention will become more apparent from the following detailed description.

In accordance with the present invention it has been discovered that particular peptides have thermoregulative properties when administered to mammals. The peptides are identified by the structure:

$R_1$-$R_2$-Trp-Ala-Val-$R_3$-His-$R_4$-$R_5$-NH$_2$  I wherein: $R_1$ is selected from the group consisting of hydrogen, an amino acid selected from the group consisting of p-Glu, Gln,Arg,Leu,Gly,Asn,Thr,Val, and Pro, and peptides having from 2 to 6 amino acids wherein the amino acids are selected from p-Glu,Gln,Arg,Leu,Gly,Asn,Thr,Val, and Pro, provided that when p-Glu is part of $R_1$, p-Glu is located at the N terminus of the peptide; $R_2$ is selected from the group consisting of D-pGlu, D-Gln and Gln; $R_3$ is selected from the group consisting of D-Ala and Gly; $R_4$ is selected from the group consisting of Phe and Leu and $R_5$ is selected from the group consisting of Met and D-Met.

The nomenclature used to describe the peptides of the present invention is in accordance with conventional practice wherein the first three letters of the trivial name of the amino acid is used to identify the amino acid and wherein the L form of any amino acid having an optical isomer is intended unless otherwise expressly indicated.

Preferred peptides within the above described group have been isolated from the skin of several anuran species and are identified by the trivial name Bombesin, Alytesin, Ranatensin and Litorin. These preferred peptides have the following structure:

| BOMBESIN | p-Glu-Gln-Arg-Leu-Gly-Asn-Gln-Trp-Ala-Val-Gly His-Leu-Met-NH$_2$ |
|---|---|
| ALYTESIN | p-Glu-Gly-Arg-Leu-Gly-Thr-Gln-Trp-Ala-Val-Gly His-Leu-Met-NH$_2$ |
| RANATENSIN | p-Glu-Val-Pro-Gln-Trp-Ala-Val-Gly-His-Phe-Met-NH$_2$ |
| LITORIN | p-Glu-Gln-Trp-Ala-Val-Gly-His-Leu-Met-NH$_2$ |

Also considered to be within the scope of the invention are intermediates having the structure:

$R_1$-$R_2$-Trp($X_2$)-Ala-Val-$R_3$-His($X_3$)$R_4$-$R_5$-$X_1$  II wherein: $R_1$, $R_2$, $R_3$, $R_4$ and $R_5$ are as previously defined: $X_1$ is selected from the class consisting of OH, OCH$_3$, esters, amides, hydrazides and benzyl ester or hydroxymethyl ester anchoring bond used in solid base synthesis and linked to a solid resin support represented by the formulae:

—O—CH$_2$-polystyrene resin and

O—CH—Benzyl-Polystyrene Resin support;

$X_2$ is a protecting group for Trp and can be formyl or hydrogen; and $X_3$ is a protecting group for His and can be Boc, tosyl, benzyl, 2,4-dinitrophenyl or benzyl.

The polystyrene resin support is preferably a copolymer of styrene with about 0.5 to 2 percent divinyl benzene as a cross linking agent which causes the polystyrene polymer to be completely insoluble in certain organic solvents.

The peptides of the invention are prepared using solid phase synthesis. The synthesis is commenced from the C-terminal end of the peptide using an α-amino protected amino acid. t-Butyloxycarbonyl (Boc) protective group can be used for all N$^α$ amino groups even though other protective groups are suitable. The solid phase synthesis procedure is started by attaching an α-amino protected Met or D-Met to a chloromethylated resin, a hydroxymethyl resin or a benzhydrylamine resin. The preparation of the hydroxymethyl resin is described by Bodanzsky et al, Chem. Inc. (London) 38, 1597–98 (1966). A chloromethylated resin is commercially available from Bio Rad Laboratories, Richmond, Calif. and the preparation of such resin is described by Stewart et al, "Solid Phase Peptide Synthesis" (Freeman & Co., San Francisco 1969), Chapter 1, pp 1–6. The preparation of benzhydrylamine resin is described in Rivier et al, J. Med. Chem. 16, 545 (1973). The α-amino protected Met or D-Met is coupled to chloromethylated resin according to the procedure of Monahan and Gilon, Biopolymer 12, pp 2513–19, 1973. Following the coupling of the α-amino protected Met or D-Met to the resin support, the α-amino protecting group is removed, such as by using trifluoroacetic acid in methylene chloride, trifluoroacetic acid alone or HCl in dioxane. The deprotection is carried out at a temperature between 0° C. and room temperature.

Other standard cleaving reagents and conditions for removal of specific α-amino protecting groups may be used as described in Schroder & Lubke, "The Peptides", 1 pp 72–75 (Academic Press 1965).

After removal of the α-amino protecting group of Met or D-Met the remaining α-amino and side chain protected amino acids are coupled step-wise in the desired order to obtain a compound of formula II or as an alternate to adding each amino acid separately to the synthesis, some of them may be coupled prior to addition to the solid phase reactor. The selection of an appropriate coupling reagent is within the skill of the art. Particularly suitable as a coupling reagent is N,N$^1$-dicyclohexylcarbodiimide.

The activating reagents used in the solid phase synthesis of the peptides are those well known in the peptide art. Examples of suitable activating reagents are: (1) carbodiimides such as N,N-diisopropyl carbodiimide, N-ethyl N$^1$-(Y-dimethylamino propyl carbodiimide; (2) cyanamides such as N,N-dibenzylcyanamide; (3) keteimines; (4) isoxazolium salts such as N-ethyl-5-phenyl isoxazolium-3$^1$-sulfonate; (5) monocyclic nitrogen containing heterocyclic amides of aromatic character containing one through four nitrogens in the ring such as imidazolides, pyrazolides, 1,2,4-triazolides. Specific heterocyclic amides that are useful include N,N$^1$-carbonyl diimidazole, N,N$^1$-carbonyl-di-1,2,4-triazole; (6) alkoxylated acetylene such as ethoxyacetylene; (7) reagents which form a mixed anhydride with the carboxyl moiety of the amino acid such as ethylchloroformate and isobutylchloroformate and (8) nitrogen-containing heterocyclic compounds having a hydroxy group on one ring nitrogen such as N-hydroxyphthalimide, N-hydroxysuccinimide and 1-hydroxybenzotriazole. Other activating reagents and their use in peptide coupling are described by Schroder & Lubke supra, in Chapter III and by Kapoor, J. Pharm. Sci., 59, pp 1–27 (1970).

Each protected amino acid or amino acid sequence is introduced into the solid phase reactor in about a four-fold excess and the coupling is carried out in a medium of dimethylformamide: methylene chloride (1:1) or in dimethylformamide or methylene chloride alone. In cases where incomplete coupling occurs the coupling procedure is repeated before removal of the α-amino protecting group and prior to the coupling of the next amino acid. The success of the coupling reaction at each stage of the synthesis is monitored by the ninhydrin reaction, as described by E. Kaiser et al, Analyt. Biochem., 34, 595 (1970).

After the desired amino acid sequence has been synthesized, the peptide is removed from the resin support by treatment with a reagent such as liquid hydrogen fluoride which not only cleaves the peptide from the resin but also cleaves all remaining side chain protecting groups and the α-amino protecting group of the terminal amino acid to obtain directly the desired peptide. Amidation of the C-terminal end is accomplished by ammonolysis of the protected peptide resin. As an alternate route, the peptide linked to the resin support may be separated from the resin by alcoholisis after which the recovered C-terminal methyl or ethyl ester is converted to the amide by ammonolysis. Any side chain protecting group may then be cleaved as previously described or by other procedures such as catalytic reduction (e.g. Pd on BaSO$_4$ using conditions which will keep the Trp moiety intact. When using hydrogen fluoride for cleaving, anisole or thioanisole is included in the reaction vessel as a scavenger.

The solid phase synthesis procedure discussed above is well known in the art and has been essentially described by Merrifield J. Am. Chem. Soc., 85, p 2149, (1964).

The peptides of the invention are at least $10^1$ to $10^4$ more effective than Neurotensin to produce hypothermia when the peptides are administered intracisternally in a mammal at a level of from about 5 to about 500 nanograms per kilograms of body weight. The peptides are not effective to produce hypothermia when administered intravenously or subcutaneously even when administered at dosage levels 10 times the effective dosage level administered intracisternally. At the above indicated dosage level, the peptides of the invention also have a strong analgesic and/or anesthetic function. The analgesic and/or anesthetic properties of the peptides are obtained without regard to the method of administration.

The following example illustrates various features of the present invention but is not intended to in any way limit the scope of the invention which is defined in the appended claims.

EXAMPLE I

A peptide having the structure:

p-Glu-Gln-Arg-Leu-Gly-Asn-Gln-Trp-Ala-Val-Gly-His-Leu-Met-NH$_2$ was synthesized by solid phase techniques. The synthesis was conducted in a step wise manner on benyhydrylamine resin. The resin was composed of fine beads (20–70 microns in diameter) of a synthetic resin prepared by copolymerization of styrene with 1 to 2 percent divinyl benzene. The benzene rings in the resin were acylated in a Friedel-Crafts reaction with benzoyl chloride or p-toluoyl chloride. The Friedel-Crafts reaction is continued until the resin contains 0.5 to 2 millimols of carbonyl per gram of resin. The carbonyl thus introduced can be replaced by a formulated amino group by the reductive aminolysis procedure of Leukart. Hydrolysis of the formyl group is performed by treatment with 6 N HCl. The benzhydrylamino group thus obtained can easily be acylated by any protected amino acid thru use of any of the known coupling agents or active esters.

In the further description of the synthesis of the peptide, the reagents will be first described by their chemical names with their common abbreviation in parenthesis. Thereafter, the reagent will be referred to by the common abbreviation. The above described peptide is prepared by the following procedure. Other peptides, described hereinafter, are synthesized by a similar technique.

Boc protected Met is linked to the benzhydrylamine resin by coupling with decylohexylcarbodiimide. After deprotection and neutralization, the peptide chain is built on the benzhydrylamine resin. Deprotection, neutralization and addition of each amino acid is performed in accordance with schedule I.←N$^\alpha$-t-butyloxycarbonyl (Boc) derivative of each amino acid is used. After deprotection of the first residue according to schedule I (steps 3 to 8 included), the N$^{60}$Boc derivative of Leu is next added along with a coupling agent which is dicyclohexylcarbodiimide (DCC) (step 9 of schedule I). P-nitrophenyl ester (ONp) is used to activate the carboxyl end of Asn. O-nitrophenyl ester can also be used for this purpose. Formyl groups can be used for the protection of the indole N-H of Trp. In this particular example, Boc xanthyl or benzhydryl Asn and Gln are used with DCC coupling in dimethylformamide (DMF).

I. Schedule for coupling of amino acids other than Asn in solid phase synthesis (5–10 g resin)

| Step | Reagents and Operations | Mix times Min. |
|---|---|---|
| 1 | CH$_2$Cl$_2$ wash 80 ml (2 times) | 3 |
| 2 | Methanol (MeOH) wash 30 Ml (2 times) | 3 |
| 3 | CH$_2$Cl$_2$ wash 80 ml (3 times) | 3 |
| 4 | 50 percent trifluoroacetic acid (TFA) containing 5 percent 1,2-ethanedithiol in CH$_2$Cl$_2$ 70 Ml (2 times) | 10 |
| 5 | CH$_2$Cl$_2$ wash 80 ml (2 times) | 3 |
| 6 | Triethylamine (Et$_3$N) 12.5 percent in CH$_2$Cl$_2$ 70 ml (2 times) | 5 |
| 7 | MeOH wash 40 ml (2 times) | 2 |
| 8 | CH$_2$Cl$_2$ wash 80 ml (3 times) | 3 |
| 9 | Boc-amino acid (10 mmoles) in 10 ml DMF (1 time) and 30 ml CH$_2$Cl$_2$ plus DCC (10 mmoles) in CH$_2$Cl$_2$ (2 M) | 30 to 120 |
| 10 | MeOH wash 40 ml (2 times) | 3 |
| 11 | Et$_3$N 12.5 percent in CH$_2$Cl$_2$ 70 ml (2 times) | 3 |
| 12 | MeOH wash 30 ml (2 times) | 3 |
| 13 | CH$_2$Cl$_2$ wash 80 ml (2 times) | 3 |

After step 13, an aliquot is taken for a ninhydrin test:

If the test is negative, go back to step 1 for coupling of the next amino acid; if the test is positive or slightly positive, go back to steps 9 through 13. Schedule I is used for coupling of each of the amino acids of the peptide to Met with the exception of Asn and Gln, when present. For peptides of the invention containing Asn and Gln steps 1 through 8 are the same and schedule II is used for the remainder of the coupling reaction: p0 II. Schedule for Boc-Asn-ONp or for any active ester coupling in solid phase synthesis (5–10 g resin)

| Step | Reagents and Operations | Mix times Min. |
|---|---|---|
| 9 | DMF wash 60 ml (3 times) | 3 |
| 10 | Boc-Asn-ONp (15 mmoles) in 20 ml DMF (1 time) | 800 |
| 11 | MeOH wash 30 ml (4 times) | 3 |
| 12 | Et$_3$N 12.5 percent in DMF 30 ml (2 times) | 3 |
| 13 | MeOH wash 30 ml (2 times) | 3 |
| 14 | CH$_2$Cl$_2$ wash 80 ml (3 times) | 3 |

After step 14, an aliquot is taken for aninhydrin test:
If the test is negative go back to step 1 for coupling of the next amino acid; if the test is positive or slightly positive, go back to steps 9 through 14. Boc xanthyl or benzhydryl Asn or Gln can be used with DCC coupling using schedule I with the exception that only DMF is used in step 9 and that step 10 also includes two DMF washes.

Cleavage of the peptides from the resin (5 grams) and deprotection of the side chain protecting groups of the peptide is performed in hydrofluoric acid (75 ml) in the presence of anisole (8 ml). After elimination of hydrofluoric acid under high vacuum, the resin-peptide is washed with ether.

The dried resin is immediately extracted with 25% acetic acid (150 ml) and diluted to 300 ml with degassed H$_2$O (N$_2$) and lyophilized. 1.2 of crude cream colored material was obtained. It was applied onto a CMC (carboxymethyl cellulose CM32 from Whatman) column (2×20 cm) equilibrated and eluted with an ammonium acetate buffer gradient 0–0.6 M NH$_4$OAc pH7.

The elution pattern as observed at 280 nm shows one major peak at an approximate concentration of 0.2 of the buffer. It is subsequently submitted to purification on partition chromatography (solvent system:n-butanol:acetic acid:water, 4:1:5) in a Sephadex G25F column (2×100 cm). Countercurrent distribution in the same solvent system can also be used. The major peak is found after elution of approximately three void volumes. After lyophilization the peptide appears homogeneous on tlc in different solvent systems.

Amino acid analysis of this material shows the expected ratio for the different amino acids.

Active esters can be used in solid phase synthesis and the classical method of synthesis can also be used to prepare the peptides of the invention.

The thermoregulative properties of the peptide were determined as follows:

Male Sprague-Dawley-CV rats weighing 180–200 grams were housed in temperature and humidity controlled quarters. The rats were fed a standard rat food ration and tap water ad libitum. After being anesthetized with ether, peptides were injected into the cisterna magna of each rat. Ten microliters of a peptide solution containing 1–1000 nanograms of the peptide were injected. Immediately following the injections, the animals were transferred to a cold room maintained at 4° C. Rectal temperatures were recorded with a thermo probe at 30 minute intervals following injection. All experiments were carried out in a randomized block design. Following analyses of variance, differences between the effect of the various peptides were determined. The peptides were dissolved in a buffer composed of 126 mM, NaCl, 6 mM KCl, 1 mM NaH$_2$PO$_4$, 0.88 mM MgSo$_4$, 1.45 mM CaCl$_2$, and 25 mM HEPES pH 7.2.

FIG. 1 shows the temperature effects of Neurotensin and the peptide prepared above in accordance with the invention on core temperature.

Figure 2:
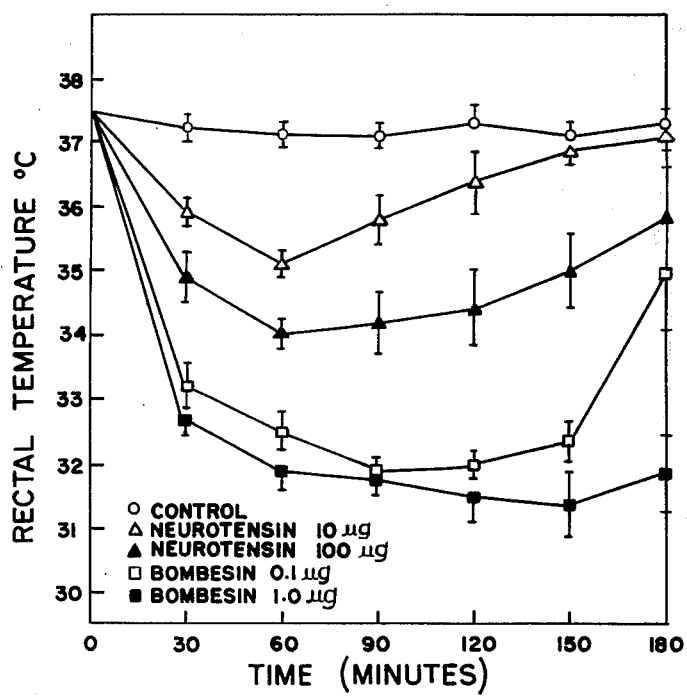

FIG. 2 shows the effect of graded doses of Neurotensin and the peptide of the invention on core temperature of rats 60 minutes following the administration. It is evident from these results that the peptide of the invention is at least 10$^4$ times more potent than Neurotensin to produce hypothermia in the cold exposed rat. Other peptides isolated from anuran skin, i.e., litorin, ranatensin and alytesin, are approximately 1%, 10% and 100% respectively as potent as the peptide described above to lower body temperature of the cold exposed rat.

The peptides of the present invention have also been observed to provide analgesic and/or anesthetic effects more potent than commonly administered analgesics. Analgesic potency of these peptides has been assessed by the "tail flick" test with mice. After intracisternal, intravenous or subcutaneous administration of the peptides, tails of mice are placed in a 58° C. water bath. In the absence of an analgesic, the mice "flick" their tails from the water.

EXAMPLE II

Further peptides of the invention were prepared in accordance with the procedure of Example I. The peptides had the following structure:

| $R_1$ | $R_2$ | $R_3$ | $R_4$ | $R_5$ |
|---|---|---|---|---|
| Des $R_1$ | D-pGlu | D-Ala | Phe | Met |
| Des $R_1$ | D-pGlu | D-Ala | Phe | D-Met |
| Des $R_1$ | D-pGlu | Gly | Leu | D-Met |
| Des $R_1$ | D-pGlu | D-Ala | Leu | D-Met |
| Des $R_1$ | D-pGlu | Gly | Phe | D-Met |
| Des $R_1$ | D-pGlu | D-Ala | Leu | Met |

The above described peptides were at least as potent as Neurotensin to produce hypothermia in cold exposed rats. The analgesic potency of these peptides, as assessed by the "tail flick" test with mice were more potent than commonly administered analgesics. The above described peptides are particularly significant in that the structure is shorter than the peptides of Example I and, hence, the peptides of Example II are easier to synthesize in large quantities.

What is claimed is:

1. A peptide useful as an analgesic and for the control of thermoregulation of mammals, said peptide having the formula:

H-D-pGlu-Trp-Ala-Val-$R_3$-His-$R_4$-$R_5$-NH$_2$ wherein: $R_3$ is selected from the group consisting of D-Ala and Gly; $R_4$ is selected from the group consisting of Phe and Leu; and $R_5$ is selected from the group consisting of Met and D-Met.

2. A peptide in accordance with claim 1 wherein $R_3$ is D-Ala, $R_4$ is Phe and $R_5$ is Met.

3. A peptide in accordance with claim 1 wherein $R_3$ is D-Ala, $R_4$ is Phe and $R_5$ is D-Met.

4. A peptide in accordance with claim 1 wherein $R_3$ is Gly, $R_4$ is Leu and $R_5$ is D-Met.

5. A peptide in accordance with claim 1 wherein $R_3$ is Gly, $R_4$ is Phe and $R_5$ is D-Met.

6. A peptide in accordance with claim 1 wherein $R_3$ is D-Ala, $R_4$ is Leu and $R_5$ is D-Met.

7. A peptide in accordance with claim 1 wherein $R_3$ is D-Ala, $R_4$ is Leu and $R_5$ is Met.

8. A method for reducing the body temperature of mammals comprising injecting a pharmaceutically effective amount of a peptide intracisternally, said peptide having the formula:

$R_1$-Gln-Trp-Ala-Val-Gly-His-$R_4$-Met-NH$_2$ wherein: $R_1$ is selected from the group consisting of p-Glu-Gln-Arg-Leu-Gly-Asn, p-Glu-Gly-Arg-Leu-Gly-Thr, p-Glu-Val-Pro and p-Glu; and $R_4$ is selected from the group consisting of Phe and Leu.

9. A method in accordance with claim 8 wherein $R_1$ is p-Glu-Gln-Arg-Leu-Gly-Asn and $R_4$ is Leu.

10. A method in accordance with claim 8 wherein $R_1$ is p-Glu-Gly-Arg-Leu-Gly-Thr and $R_4$ is Leu.

11. A method in accordance with claim 8 wherein $R_1$ is p-Glu-Val-Pro, and $R_4$ is Phe.

12. A method in accordance with claim 8 wherein $R_1$ is p-Glu, and $R_4$ is Leu.

13. A method for reducing the body temperature of mammals comprising injecting a pharmaceutically effective amount of a peptide intracisternally, said peptide having the formula:

H-D-pGlu-Trp-Ala-Val-$R_3$-His-$R_4$-$R_5$-NH$_2$ wherein: $R_3$ is selected from the group consisting of D-Ala and Gly; $R_4$ is selected from the group consisting of Phe and Leu and $R_5$ is selected from the group consisting of Met and D-Met.

14. A method in accordance with claim 13 wherein $R_3$ is D-Ala, $R_4$ is Phe and $R_5$ is Met.

15. A method in accordance with claim 13 wherein $R_3$ is D-Ala, $R_4$ is Phe and $R_5$ is D-Met.

16. A method in accordance with claim 13 wherein $R_3$ is Gly, $R_4$ is Leu and $R_5$ is D-Met.

17. A method in accordance with claim 13 wherein $R_3$ is Gly, $R_4$ is Phe and $R_5$ is D-Met.

18. A method in accordance with claim 13 wherein $R_3$ is D-Ala, $R_4$ is Leu and $R_5$ is D-Met.

19. A method in accordance with claim 13 wherein $R_3$ is D-Ala, $R_4$ is Leu and $R_5$ is Met.

20. A method for inducing analgesia in mammals comprising introducing into said mammal a pharmaceutically effective amount of a peptide, said peptide having the formula:

$R_1$-Gln-Trp-Ala-Val-Gly-His-$R_4$-Met-NH$_2$ wherein: $R_1$ of said peptide is selected from the group consisting of p-Glu-Gln-Arg-Leu-Gly-Asn, p-Glu-Gly-Arg-Leu-Gly-Thr, p-Glu-Val-Pro and p-Glu, and $R_4$ is selected from the group consisting of Phe and Leu.

21. A method in accordance with claim 20 wherein $R_1$ is p-Glu-Gln-Arg-Leu-Gly-Asn and $R_4$ is Leu.

22. A method in accordance with claim 20 wherein $R_1$ is p-Glu-Gly-Arg-Leu-Gly-Thr and $R_4$ is Leu.

23. A method in accordance with claim 20 wherein $R_1$ is p-Glu-Val-Pro, and $R_4$ is Phe.

24. A method in accordance with claim 20 wherein $R_1$ is p-Glu, and $R_4$ is Leu.

25. A method for inducing analgesia in mammals comprising introducing into said mammal a pharmaceutically effective amount of a peptide, said peptide having the formula:

H-D-p-Glu-Trp-Ala-Val-$R_3$-His-$R_4$-$R_5$-NH$_2$ wherein: $R_3$ is selected from the group consisting of D-Ala and Gly; $R_4$ is selected from the group consisting of Phe and Leu and $R_5$ is selected from the group consisting of Met and D-Met.

26. A method in accordance with claim 25 wherein $R_3$ is D-Ala, $R_4$ is Phe and $R_5$ is Met.

27. A method in accordance with claim 25 wherein $R_3$ is D-Ala, $R_4$ is Phe and $R_5$ is D-Met.

28. A method in accordance with claim 25 wherein $R_3$ is Gly, $R_4$ is Leu and $R_5$ is D-Met.

29. A method in accordance with claim 25 wherein $R_3$ is Gly, $R_4$ is Phe and $R_5$ is D-Met.

30. A method in accordance with claim 25 wherein $R_3$ is D-Ala, $R_4$ is Leu and $R_5$ is D-Met.

31. A method in accordance with claim 25 wherein $R_3$ is D-Ala, $R_4$ is Leu and $R_5$ is Met.

* * * * *